United States Patent [19]

Poncy et al.

[11] Patent Number: 4,593,699

[45] Date of Patent: Jun. 10, 1986

[54] STERILE COVER FOR INTRAOPERATIVE ULTRASONIC DIAGNOSTIC DEVICES AND METHOD AND KIT FOR PROVIDING SAME

[76] Inventors: Richard P. Poncy, 5105 Woodland Lakes Dr.; Mark P. Poncy, 5125 Woodland Lakes Dr., both of Palm Beach Gardens, Fla. 33410

[21] Appl. No.: 503,838

[22] Filed: Jun. 13, 1983

[51] Int. Cl.$^4$ .............................................. A61B 10/00
[52] U.S. Cl. ...................................... 128/660; 206/305
[58] Field of Search ................... 128/660–663, 128/132 R; 206/212, 438, 205, 305

[56] References Cited

U.S. PATENT DOCUMENTS

| | | | |
|---|---|---|---|
| 2,677,965 | 5/1954 | Saffir | 374/208 |
| 3,017,705 | 1/1962 | Peters | 128/132 R X |
| 3,779,234 | 12/1973 | Eggelton et al. | |
| 4,069,913 | 1/1978 | Harrigan | 128/132 R X |
| 4,224,936 | 9/1980 | Cox | 128/132 R |
| 4,349,033 | 9/1982 | Eden | |

OTHER PUBLICATIONS

Taylor et al., "A High Resolution Transrectal Ultrasonographic System" Ultra Med. Bio., vol. 5, No. 2, 1979, pp. 128-138.

Primary Examiner—Kyle L. Howell
Assistant Examiner—Francis J. Jaworski
Attorney, Agent, or Firm—Lane and Aitken

[57] ABSTRACT

A sterile cover for a sonic probe and connecting cable of a sonic imaging instrument includes (1) a flexible sleeve, open at both ends and having a sterile exterior surface, covering at least a portion of the cable and all but a distal end of the probe and (2) a flexible sheath, open at one end and closed at the other end and having a sterile exterior surface, that fits over a portion of the sleeve and covers at least the distal end of the probe. A method and kit for providing a sterile cover is also described.

18 Claims, 7 Drawing Figures

STERILE COVER FOR INTRAOPERATIVE ULTRASONIC DIAGNOSTIC DEVICES AND METHOD AND KIT FOR PROVIDING SAME

BACKGROUND OF THE INVENTION

This invention relates to a sterile cover for an ultrasonic probe inserted through the outer integument of the body, as well as a method and a kit for providing the cover.

There is now in existence ultrasonic diagnostic equipment for providing images of tissue in organs within the body. Basically, this equipment operates by transmitting high frequency pulses of sound into the body, detecting the pattern of reflection of this sonic energy, and translating this information into a visual image. The advantage of this technique is that the images of the tissue or organs inside the body can be obtained without disrupting the integrity of the body.

More recently, it has been found that better images can be obtained if the sonic probe or transducer of the equipment is inserted through the outer integument of the body. Ultrasonic diagnostic probes have been designed for insertion through the skin of the patient and, in the case when an image of the brain is desired, even through the skull. When such a probe is used, it is necessary that the procedure be carried out under asceptic conditions and that the sterility of the probe, the connecting cable, and all persons and other devices coming into actual or approximate contact with the probe must be maintained. One way that sterility has been maintained is to sterilize the probe and the cable after each use, but this technique is not practical. The sterilization procedure, including the necessary controls to ensure the effectiveness of the sterilization procedure, requires one to eight days. Of course, during this sterilization period, no further diagnoses can be made with the probe. This problem can be avoided by the use of multiple substitute probes, but the probes themselves cost over $10,000.00 each and most hospitals cannot afford to purchase a large number. Another inadequate solution to the problem of sterilization has been to cover the probe and cable in whatever sterile materials are available, such as surgical gloves. Thus, there is a need in the art for an effective, convenient, and inexpensive way to provide for and maintain the sterilization of sonic probes and connecting cables.

SUMMARY OF THE INVENTION

In accordance with the present invention, a sterile cover is provided for a sonic probe and connecting cable of a sonic imaging instrument, as well as a method and kit for providing the cover. The sterile cover includes a flexible sleeve which can cover at least a portion of a connecting cable and all but a distal end of a transducer probe, and a flexible sheath that fits over a portion of the sleeve and covers at least the distal end of the probe. The method for providing the sterile cover includes the step of inserting the probe through an untapered end of the sleeve until all but the distal end of the probe and at least a portion of the cable is covered by the sleeve, followed by the step of applying the sheath to cover at least the distal end of the probe. A kit is also disclosed which includes a sterile package which contains the sleeve and the sheath.

DESCRIPTION OF THE PREFERRED EMBODIMENTS

Figure 1:
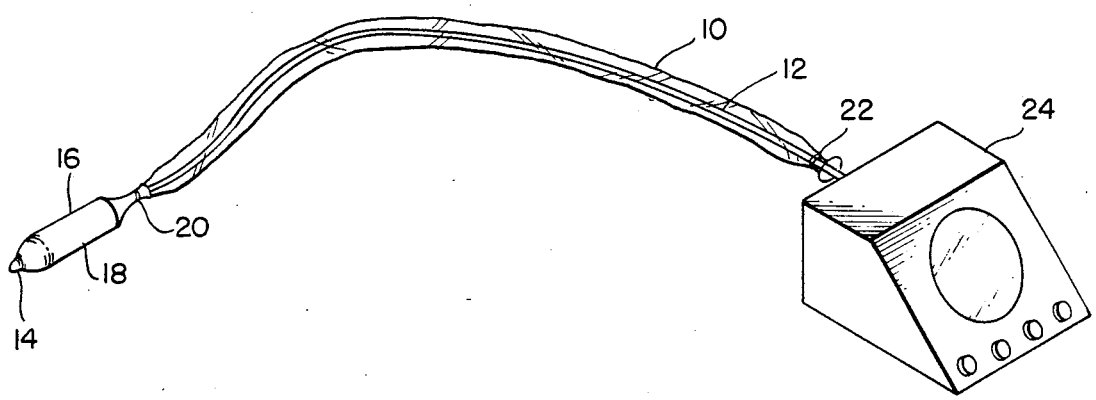
FIG. 1 is a perspective view of the sterile cover as applied to the sonic probe and connecting cable of a sonic imaging instrument.
Figure 4:
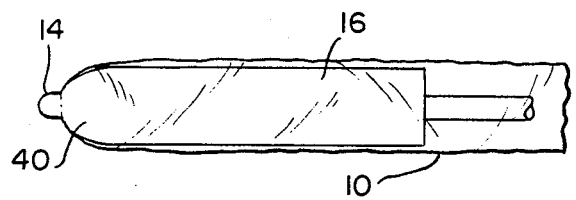
FIG. 4 is a perspective view depicting the manner in which the sleeve covers a probe and cable.

The sterile cover as applied to a probe and cable is depicted in FIG. 1. The sterile cover comprises a sleeve 10 which covers the major portion of cable 12, and, as best shown in FIG. 4, all but the distal end 14 of a probe 16. Sheath 18 fits over sleeve 10 and covers at least the distal end 14 of probe 16. In the preferred embodiment depicted in FIG. 1, the sheath covers all of the probe and a portion of the cable 12, and an elastic band 20 is applied to the portion of the sheath that covers the cable. A second elastic band 22 can be applied at the end of the sleeve nearest to the sonic imaging instrument 24.

Figure 3:
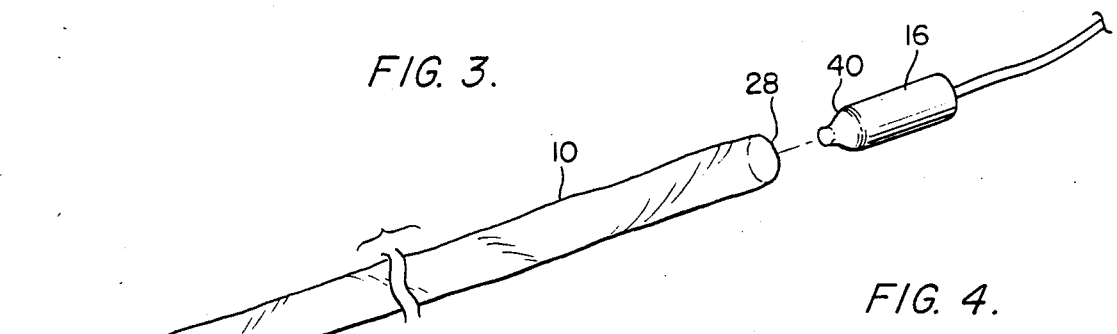
FIG. 3 is a perspective view of a sonic probe and connecting cable before being inserted into the sleeve.

The sleeve 10 is flexible and can be made of any suitable sterilizable plastic, such as polyethylene. As depicted in FIGS. 1 and 3, it has openings at both ends and is elongated to cover at least a portion of cable 12. The circumference of the sleeve should be slightly larger than that of the probe, and one end of the sleeve is preferably tapered to correspond with the tapered shape 40 of the probe. As depicted in FIG. 3, the opening 26 at the tapered end preferably has a circumference just large enough to allow the passage of the distal end 14 of the probe. The sleeve can be seamed or unseamed, since no ultrasonic sound waves will need to be passed through it. At least the exterior surface of the sleeve is sterile.

Figure 5A:
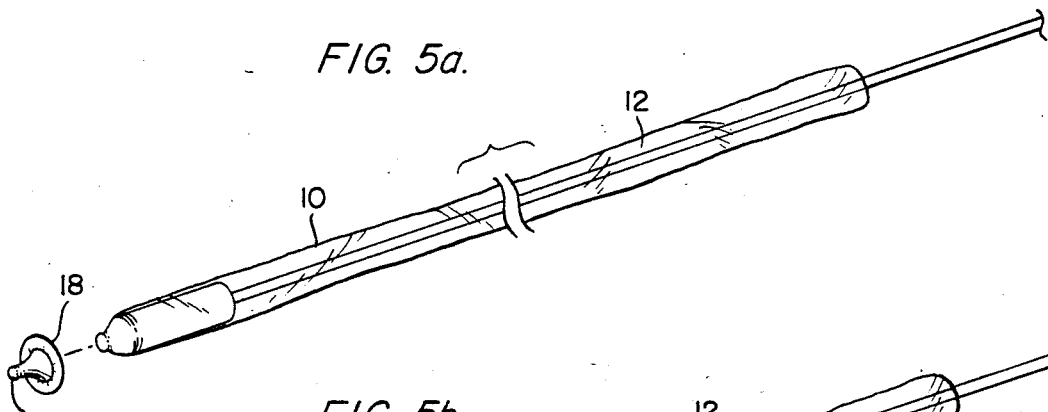
FIG. 5(a) is a perspective view depicting a sheath before being applied to the distal end of the probe.
Figure 5B:
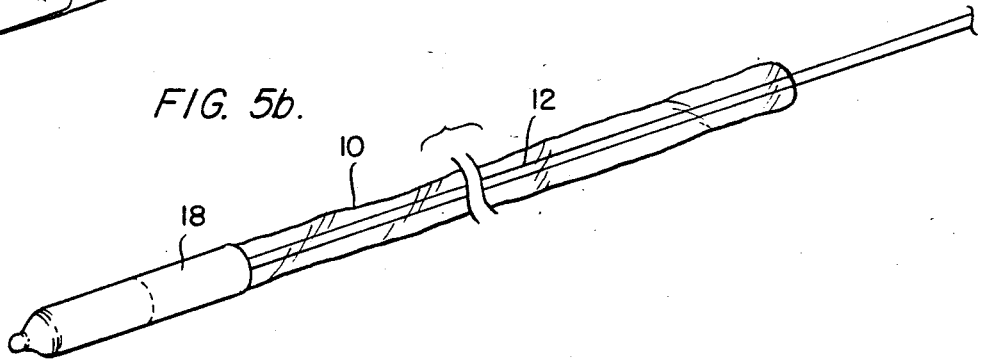
FIG. 5(b) is a perspective view depicting the the manner in which the sheath covers the sleeve and the probe.

The sheath 18 is designed to fit snugly around the probe and preferably to extend a short distance behind the probe, to thus cover a portion of the cable, as best depicted in FIG. 5(b). It has a closed end and an open end, and the closed end is shaped to mate with the tapered shape 40 of the probe. The tip 30 of the sheath is nipple shaped in order to receive the distal end 14 of the probe. The sheath should be flexible and sterilizable, and is preferably composed of an elastomer to provide the snug fit with the probe.

The part of the probe that is inserted through the integument of the body and into the body proper is the distal end 14. In order for a clear image to be generated, it is important that this distal portion, although covered, be wrapped by a completely homogenous, air-free, regular and non-seamed surface. By providing that the sheath is shaped to mirror the 3-dimensional configuration of the probe in an exact fashion, the elimination of air between the probe and the sheath is facilitated. The elimination of air is also facilitated by first rolling sheath 18, as depicted in FIG. 5a, and applying the sheath by unrolling it onto the probe. The production of an air free contact between the probe and sheath is further facilitated by the application of sound-conducting jelly at the contacting surfaces between the distal end 14 and sheath 18.

An economic advantage of the two-part sterile cover system of the present invention is that, while the distal end 14 of the probe requires a non-seamed cover, the body of the probe and cable can be covered with materials that do not meet this requirement. Thus, the invention combines the economy of what may be a seamed, flexible plastic sleeve 10 with the high quality sheath 18 for the distal end 14 of the probe. Theoretically, it would be possible to produce a molded latex cover of high quality which would cover both the distal end of the probe and the connecting cable 12, but such a cover would be impractical, since the molds and processes necessary to produce such a cover would be extremely expensive, and the resulting product would be unwieldy. Further, such an inordinately long latex cover could not be rolled up, so that some of the advantages of the present invention, i.e., the elimination of air around distal end 14 and the facilitation of placing the sheath 18 on the probe, would be difficult to achieve.

In order to achieve the most accurate measurements from the sonic imaging equipment, the homogeneity of the sheath 18 is important. When latex products are normally molded, they are released from their mold with the aid of a particulate powdiferous substance. If such a product were used to cover the distal end 14, the powder would decrease the accuracy of the sonic imaging equipment. Moreover, such powder is harmful to body tissues, and granuloma and adhesion formation may occur in response to particulate contamination of a surgical wound. In carrying out the present invention, it has been found that these problems can be overcome by increasing the dwell time of the molding process used to produce sheath 18 so that the thickness of the cover is increased. This thicker cover may be stripped from its mold without a powdiferous releasing agent, and thus a latex sheath 18 with the proper requirements can be obtained.

In a preferred embodiment, a semi-rigid O-ring can be attached to or incorporated in the open end of sheath 18. The O-ring may be made of a phenolic material, a metal, or any other suitable semi-rigid material. Preferably the diameter of the O-ring is slightly larger than that of the probe body and the width of the wall of the O-ring is less than ¼ inch and, preferably, this width is extremely small. The O-ring can be attached to or inserted in the sheath 18 in any suitable manner. One way is to place the O-ring onto the sheath 18 and entrap the O-ring in the sheath in the manufacturing process of rolling the sheath. By incorporating or attaching the O-ring, the mouth of sheath 18 will be held open to facilitate the insertion of the probe, and the unrolling of the sheath along the probe body will be facilitated.

Figure 5C:
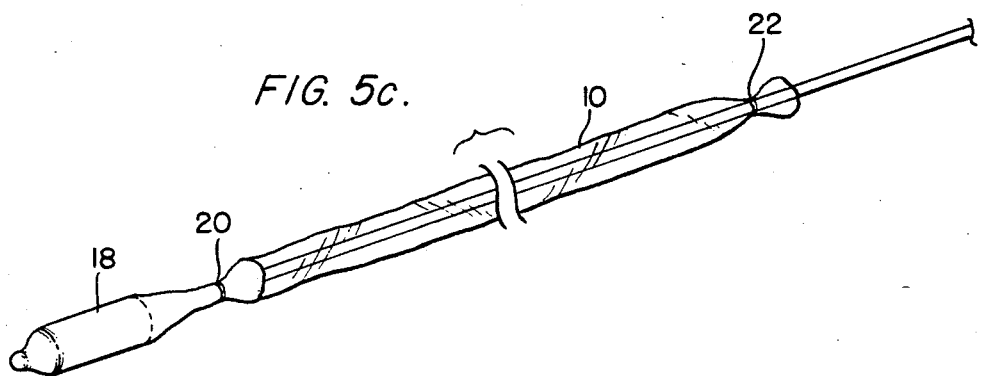
FIG. 5(c) is a perspective view of an applied sterile cover in accordance with the invention.

As depicted in FIG. 5(b), sheath 18 will preferably extend beyond the body of the probe to thus cover a portion of the cable 12. When the sheath is so extended, the extended portion can be drawn in towards the cable by using band 20 as depicted in FIG. 5(c). By drawing the extended portion in in this manner, the possibility that the extended portion will interfere with the manipulation of the probe body is eliminated, and the sterile field is better defined and becomes more difficult to accidentally contaminate. The use of the O-ring in sheath 18 can help to maintain band 20 in place.

Figure 2:
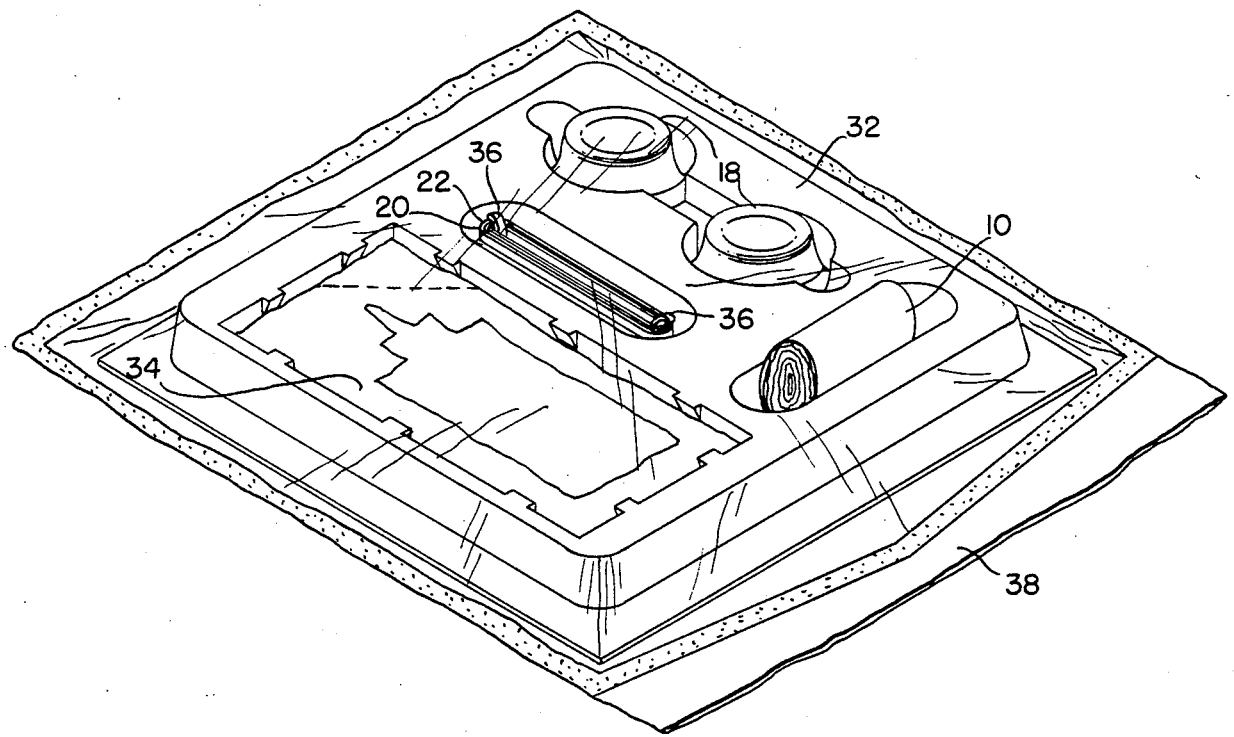
FIG. 2 is a perspective view of a kit usable to provide the sterile cover depicted in FIG. 1.

The method for applying the sterile cover is as follows. Prior to the application of the sterile cover, the probe is preferably disinfected and placed in a sterile basin until the imaging process takes place. When the imaging process is to commence, the sleeve 10, which can originally be in a rolled storage position as depicted in FIG. 2, is extended and probe 16 is inserted through the untapered end 28 as depicted in FIG. 3. When fully inserted in the sleeve, the probe will stop as its tapered end contacts the tapered end of the sleeve. As depicted in FIG. 4, the distal end 14 of the probe will then protrude through the small terminal slit at the end of the sleeve. Preferably, the sleeve 10 is banded with band 22 to secure the sleeve in position and to ensure maintenance of sterility.

It has been noted that, in order for the sonic imaging equipment to generate a clear image, the distal end of the probe should be covered by an air-free surface. In order to facilitate the production of an air-free environment between the distal end 14 and the sheath 18, sound conducting jelly is applied to the distal end of the probe. A suitable sound conducting jelly is Ultra/Phonic, which is distributed by Pharmaceutical Innovations, Inc. of Newark, N.J. Application of the jelly to this region can be effected either by placing the jelly on the distal end 14 or by placing the jelly into the nipple-shaped tip 30 of the sheath. The application of the jelly helps to eliminate the possibility of air being trapped between the sheath and distal end of the probe.

Next, sheath 18, which is advantageously provided in a rolled fashion as depicted in FIG. 5(a), is first positioned on the distal end 14 of the probe and then unrolled along the body of the probe until the probe is completely covered. It can be seen that the tapering of sleeve 10 near opening 26 ensures that the sleeve will not be pushed off the body of the probe during the unrolling step of the sheath. In a preferred embodiment, sheath 18 is long enough to extend beyond probe 16, and the extended portion can be banded with band 20.

In another embodiment, an outer sheath is applied in the same manner as the first, after sound conducting jelly is applied to the exterior of tip 30 of the first sheath or to the interior of a corresponding nipple-shaped portion of the outer sheath.

In a hospital environment, it will be convenient for the circulating nurse, who is not sterile, to apply the sleeve 10 to the probe and cable by grasping the sleeve at only the untapered end 28 and then inserting the probe 16 into this end of the sleeve. Then, while still grasping the sleeve at only the untapered end, the circulating nurse can draw the sleeve over the probe and over the connecting cable until the tapered end of the sleeve engages the mating conical end of the probe. Since the circulating nurse touches only the untapered end of the sleeve, this is the only portion of the sleeve which is rendered unsterile by the procedure performed by the circulating nurse. The sterile nurse, wearing sterile surgical gloves, can then apply the sheath 18 to the probe over the sleeve.

Upon completion of the ultrasonic scan and imaging process, the sheath and sleeve can be removed and disposed of. Preferably, after removal of the used sheath and sleeve, the probe is cleaned by removing the sound conducting jelly with a damp cloth or sponge. The probe and instrument are immediately ready for reuse after the application of a new sterile sleeve and sheath to the probe and cable.

In accordance with the present invention, the component parts of the sterile cover are conveniently enclosed in a sterile kit, as depicted in FIG. 2. As depicted in the drawing, the kit includes a molded plastic tray 32 which is provided with recessions to hold the component parts of the sterile cover. Thus, recessions are provided for sleeve 10, sheaths 18, bands 20, 22, and a package of sound conducting jelly 34. Bands 20, 22 are maintained in place by drawing them around protruding clips 36. All of the component parts as well as the tray 32 are sterilized, and these parts are enclosed in a sterile container, such as plastic bag 38. In a preferred embodiment, a lower part of the recession for sheaths 18 is designed to suspend the sheath to enable the tips 30 of the sheaths to be inverted and sufficiently open so that sound conducting jelly can be inserted into the tips 30 while the sheaths are still in the tray. Tray 32 can be made of any suitable, substantially rigid and sterilizable material. Bag 38 is preferably clear and flexible and can be provided with a means to facilitate opening without the need of a cutting instrument.

While there have been described what are considered to be preferred embodiments of this invention, it will be obvious to those skilled in the art that various changes and modifications may be made therein without departing from the invention. It is intended that the present description cover all such changes and modifications as may be within the spirit and scope of the invention.

We claim:

1. A method of providing a sterile cover over a sonic probe and flexible connecting cable of a sonic imaging instrument, said cable extending between said probe and a sonic imaging instrument, comprising placing a flexible sleeve, open at both ends and having a sterile exterior surface, over said cable and said probe with a distal end of said probe protruding from one end of said sleeve, and placing a flexible sheath, open at one end and closed at the other end and having a sterile exterior surface, over at least the distal end of said probe and over said one end of said sleeve.

2. The method according to claim 1, wherein said one end of said sleeve is tapered to define the opening at said one end of said sleeve to have a circumference shorter than the circumference of the remainder of said sleeve, and wherein said placing step includes placing said sleeve onto said probe and said cable by inserting said probe into the end of said sleeve opposite from said one end and drawing said sleeve over said probe and over said cable until the tapered portion of said sleeve at said one end engages a tapered shape of said probe.

3. The method according to claim 1, further comprising the steps of rolling up said sheath prior to placing it on said probe, and placing said sheath on said probe by positioning a tip of said sheath on said distal end of said probe and unrolling said sheath over said probe and over said one end of said sleeve.

4. The method according to claim 1, further comprising the step of applying sound conducting jelly to said distal end of said probe or to the interior of a tip of said sheath prior to said placing said sheath over said distal end.

5. The method according to claim 1, further comprising the step of banding an end of said sleeve that is opposite from said one end of said sleeve.

6. The method according to claim 1, wherein said sheath covers all of said probe and a portion of said connecting cable, further comprising the step of banding said sheath at a portion of said sheath which covers said cable.

7. The method according to claim 1, further comprising the steps of applying an outer sheath over said sheath after first applying sound conducting jelly to the exterior of a tip of said sheath or the interior of a tip of said outer sheath.

8. The method according to claim 1, further comprising the step of removing and discarding said sheath and said sleeve after a sonic imaging procedure has been completed.

9. A kit for providing a sterile cover over a sonic probe having a distal end with a predetermined shape and the cable connecting said probe to a sonic imaging instrument, said kit comprising:
a sleeve tapered at one end to define an opening at said one end substantially smaller than the passage through the remainder of said sleeve, said taper being shaped to correspond with the shape of the distal end of said probe, said sleeve being sufficiently flexible to bend to a substantial degree of curvature without damage, being open at both ends and having a sterile exterior surface;
a sheath at one end and closed at another end and having a sterile exterior surface; and
a package having a sterile interior, said package enclosing said sleeve and said sheath so that the sterile condition of said sheath and sleeve is maintained,
wherein said sleeve is adapted to cover at least a portion of said cable and all but said distal end of said probe and said sheath is adapted to fit over a portion of said sleeve and cover at least said distal end of said probe, the closed end of said sheath being shaped to fit with the distal end of said probe and correspond to the shape of the tapered end of said sleeve so that the tapered end of said sleeve and the closed end of said sheath fit together when mounted on said probe.

10. The kit according to claim 9, wherein said sleeve is tapered at one end adapted to be adjacent to said distal end of said probe, such that the tapered portion of said sleeve mates with a tapered shape of said probe.

11. The kit according to claim 9, wherein said sheath is elastomeric and produced in a molding process without use of a powdiferous releasing agent.

12. The kit according to claim 9, further comprising an amount of sound conducting jelly enclosed in said package, said jelly adapted to be applied between said distal end and at least a tip of said sheath.

13. The kit according to claim 9, wherein said sheath is adapted to cover all of said probe and at least a portion of said cable, and wherein said kit further comprises a first band adapted to constrict a portion of said sheath that covers said cable.

14. The kit according to claim 13, further comprising a second band adapted to constrict an end of said sleeve that is opposite to said one end.

15. The kit according to claim 9 wherein said open end of said sheath comprises an O-ring.

16. The kit according to claim 9, further comprising an outer sheath adapted to cover at least a tip of said sheath.

17. The kit according to claim 9 wherein a tray is provided with recesses which correspond to component parts of said kit to hold said parts.

18. The kit according to claim 17 wherein a recess in said tray for said sheath maintains a tip of said sheath in an inverted, open position so that sound conducting jelly can be dispensed into said tip while the sheath is disposed in said tray.

* * * * *